United States Patent [19]
Gardner

[11] Patent Number: 5,358,112
[45] Date of Patent: Oct. 25, 1994

[54] DENTAL BUR STORAGE DEVICE

[76] Inventor: Forrest S. Gardner, 10213 Hopeland Ave., Downey, Calif. 90241

[21] Appl. No.: 81,801

[22] Filed: Jun. 23, 1993

[51] Int. Cl.⁵ .............................................. A61C 1/14
[52] U.S. Cl. ................... 206/369; 206/63.5; 206/443; 211/69
[58] Field of Search ............... 206/368, 369, 63.5, 206/443; 211/69, 74

[56] References Cited

U.S. PATENT DOCUMENTS

| | | | |
|---|---|---|---|
| 1,104,650 | 7/1914 | Fries | 211/69 X |
| 1,352,490 | 9/1920 | Wilkins | 211/69 |
| 1,965,032 | 7/1934 | Davey | 211/69 |
| 3,349,937 | 10/1967 | Duff et al. | 211/69 X |
| 4,284,603 | 8/1981 | Korom | 211/74 X |
| 4,306,862 | 12/1981 | Knox | 206/63.5 X |

Primary Examiner—Paul T. Sewell
Assistant Examiner—Jacob K. Ackun, Jr.
Attorney, Agent, or Firm—Price, Gess & Ubell

[57] ABSTRACT

A dental bur storage device that includes a base member and a lid. The base member includes a bottom floor, a first support floor with a plurality of support apertures that is parallel to the bottom floor, and a second support floor with a plurality of support apertures that is parallel to the first support floor. The burs are secured in the storage device by placing them through the support apertures of the first and second support floor, which support the burs in a perpendicular position to the bottom floor. The lid is then closed to the base member. The lid, when closed, is of a dimension above the base member to fit burs in the storage device and also prevent them from falling out. The base member and lid also have open parallel sides to enable the burs to be sterilized while remaining in a storage mode. The storage device, with stored burs, is inserted into a cleaning apparatus, which is able to reach the burs through the open sides.

2 Claims, 2 Drawing Sheets

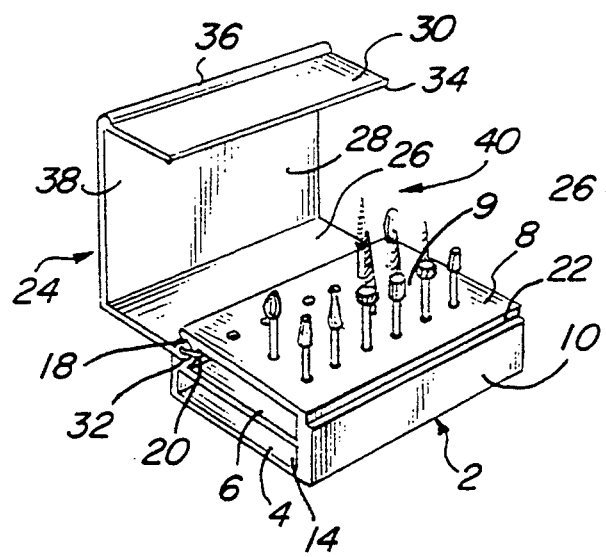
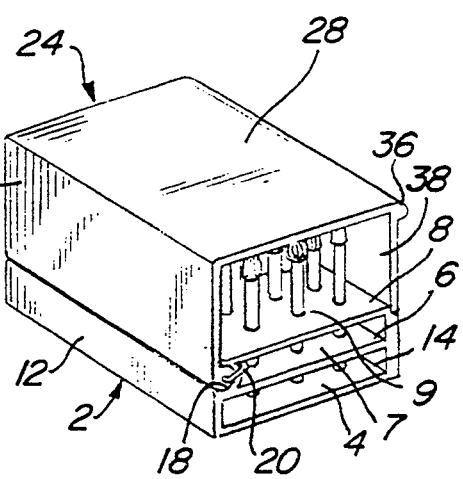
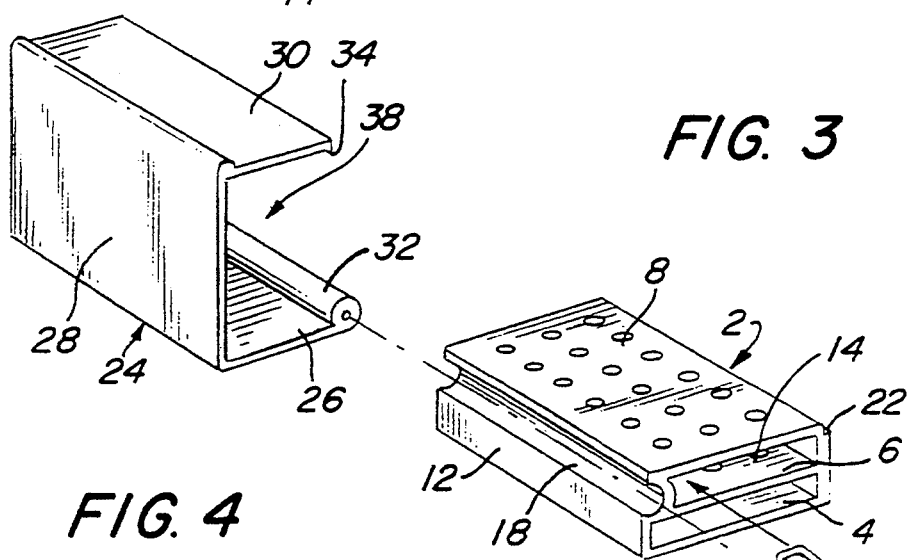
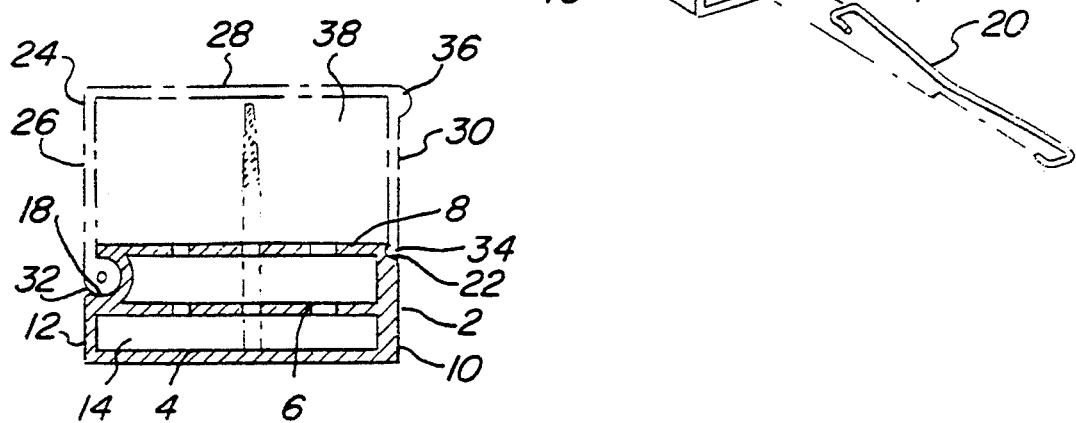

DENTAL BUR STORAGE DEVICE

BACKGROUND OF THE INVENTION

1. Field of the Invention

This invention relates to a storage device to be used by dentists to store their dental burs and more particularly, enable dental burs to be sterilized while in a storage mode.

2. Description of Related Art

Dental burs stored in some previous storage devices must be removed by hand to be sterilized. The technician's extensive handling of the burs creates a high risk of the technician cutting him or herself with a bur and possibly becoming infected with a disease.

Prior dental bur storage devices may not have lids which may help to secure the burs inside the storage device. By securing the dental burs inside the storage device, the burs can be sterilized without removing them from the storage device. In addition, a lid can help prevent technicians from accidentally coming into contact with the burs. Accidental contact with the burs can cause the burs to need to be re-sterilized and also possibly cut the technicians and infect him or her with a disease.

Prior dental bur storage devices can also be expensive to manufacture. They are usually individually molded or require extensive assembly.

The prior art has recognized the importance of creating an inexpensively manufactured dental bur storage device that helps to protect technicians from accidentally becoming infected with contagious diseases while sterilizing dental burs.

SUMMARY OF THE INVENTION

The present invention is a storage device for dental burs which has the ability to lock dental burs inside the storage device. The burs are locked inside the storage device by use of a base member that includes a bottom floor, a first support floor with a plurality of support apertures that is parallel to the bottom floor, and a second support floor with a plurality of support apertures that is parallel to the first support floor. The burs are placed through the support apertures of the first and second support floors, which support the burs in a position perpendicular to the bottom floor. In addition, a lid is closed over the base member. When the lid is closed, it is of such a dimension relative to the base member that dental burs can be stored in the storage device, and prevented from falling out.

The present invention also allows the burs to be sterilized while in a storage mode. This is accomplished by having open parallel sides on the member base and open parallel sides on the lid. With the burs inside the storage device, the device is then placed into a cleaning apparatus such as an autoclave and an ultrasonic cleaning bath. The open sides of the storage device allow the cleaning substance to reach the stored burs.

The lid also prevents a user from accidentally coming into contact with the burs, which could result in the user accidentally cutting themselves on the burs or causing the burs to need to be re-sterilized.

The present invention is manufactured by an inexpensive method. The storage device is manufactured by providing an extruded elongated base member and an extruded elongated lid which are cut into pre-determined sections. Support apertures are then drilled into the base members. The lids are then attached to the base members and reinforced by a resilient pin.

BRIEF DESCRIPTION OF THE DRAWINGS

The exact nature of this invention, as well as its objects and advantages, will become readily apparent upon reference to the following detailed description when considered in conjunction with the accompanying drawings, in which like reference numerals designate like parts throughout the figures thereof, and wherein:

FIG. 1 is a perspective view of an open dental bur storage device;

FIG. 2 is a perspective view of a closed dental bur storage device;

FIG. 3 is an exploded view of the dental bur storage device, including the lid, the resilient pin, and the base member;

FIG. 4 is a sectional view of the base member showing the bottom floor, first support floor, second support floor, and the first side opening;

DESCRIPTION OF THE PREFERRED EMBODIMENTS

Figure 5:
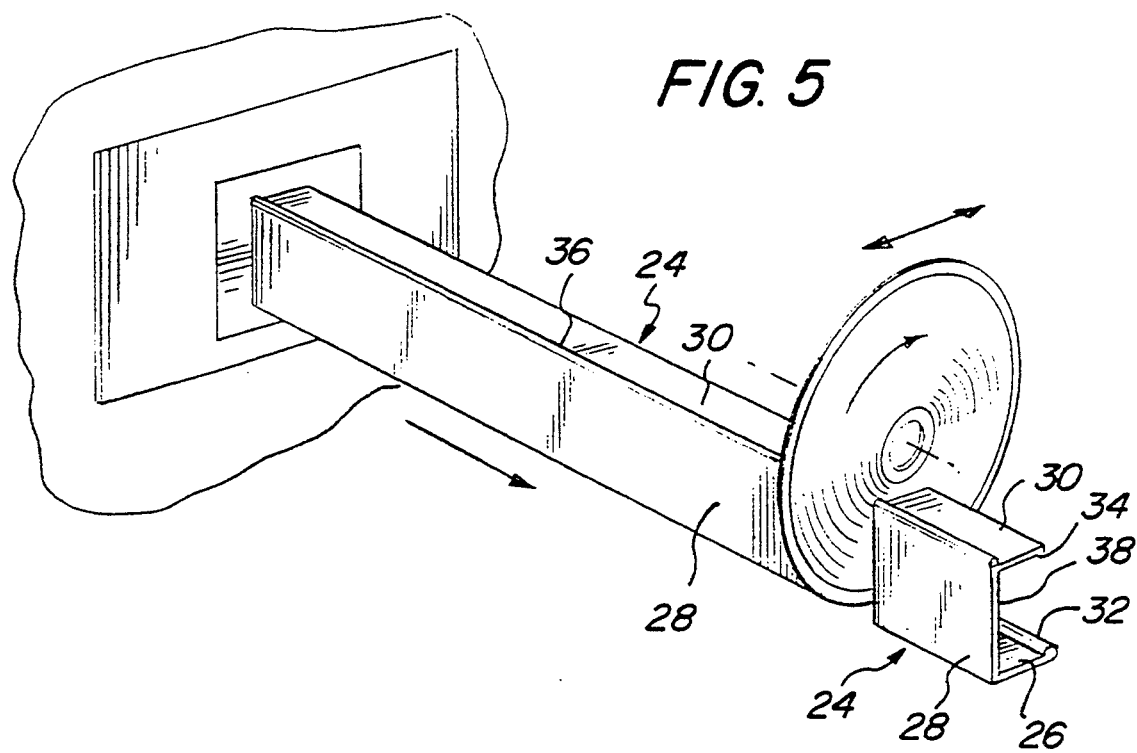
FIG. 5 is a perspective view of an extruded elongated base member being cut into predetermined sections by a saw blade.

The following description is provided to enable any person skilled in the art to make and use the invention and sets forth the best modes contemplated by the inventor of carrying out his invention. Various modifications, however, will remain readily apparent to those skilled in the art, since the generic principles of the present invention have been defined herein specifically to provide an inexpensively manufactured dental bur storage device that removably locks dental burs inside the storage device and allows the burs to be sterilized while in a storage mode.

The storage device is constructed to store dental burs, which are pointed and threaded tools used by dentists for boring and drilling. The dental bur storage device may be fabricated from aluminum which is recyclable and therefore can be sold internationally as some countries charge fines for use of non-recyclable products. It will be obvious to those skilled in the art that various equivalent materials may be utilized to fabricate the dental bur storage device. The dental bur storage device is also available in variable colors. Some dentist have more than one office and the color coding is helpful for them in keeping the tools separate.

FIG. 1 illustrates an open dental bur storage device that includes a base member 2 and a lid 24. The base member 2, as best shown in FIGS. 1 and 4, includes a bottom floor 4, a first support floor 6 with a plurality of support apertures 7 that is parallel to the bottom floor 4, a second support floor 8 with a plurality of support apertures 9 that is parallel to the first support floor 6, a front wall 10, a back wall 12, a first open side 14, and a second open side 16 parallel to the first open side 14. The base member 2 also includes an axle socket 18 at the cornice of the back wall 12. The axle socket 18 is closed enough to require an axle 32 be inserted through a side of the axle socket 18. The base member 2 also has an overcentered locking lip 22 at the cornice of the front wall 10.

The lid 24, as best shown in FIGS. 1, 2 and 3, includes a top front wall 30, a ceiling 28, a top back wall 26, and an axle 32 at the end of the top back wall 26, which is inserted into an end of the axle socket 18. The lid 24 also includes a first lip 34 at the end of the top front wall 30 facing inside the lid 24, a second lip 36 at the outside cornice of the top front wall 30, a third open side 38, and a fourth open side 40 parallel to the third open side 38.

As shown in FIGS. 1 and 3, the lid 24 is reinforced to the base member 2 by a resilient pin 20 which is partly inserted into the ends of the axle 32 and is wrapped through the base member 2, behind the axle socket 18 underneath the second support floor 8.

As shown in FIGS. 1 and 2, the dental bur storage device secures burs within the storing device. The burs are supported in a perpendicular position to the bottom floor 4 by inserting the burs through support apertures 7, 9 of the first and second support floors 6, 8. The lid 24 is then closed to the base member 2, which prevents the burs from falling out of the base member 2. When the lid 24 is closed to the base member 2, the ceiling 28 is of a dimension above the base member 2 to fit burs inside the storage device and prevent them from falling out of the storage device. The lid 24 is locked to the base member 2 by pressing the first lip 34 of the lid 24 over the over-center locking lip 22 of the base member 2.

The dental bur storage device also allows the stored burs to be sterilized without removing the burs from the storage device. The storage device with enclosed burs is placed into a cleaning apparatus such as an autoclave and an ultrasonic cleaning bath. The open sides 14, 16, 38, and 40 enable the ultrasonic energy of the cleaning bath to reach the burs and remove any debris. This is an effective method of sterilizing the burs because the burs do not have to be physically removed and replaced, before and after cleaning. Less physical handling of the burs, creates a lower risk of a technician cutting his or herself on the burs and possibly infecting themselves with a disease.

Figure 6:
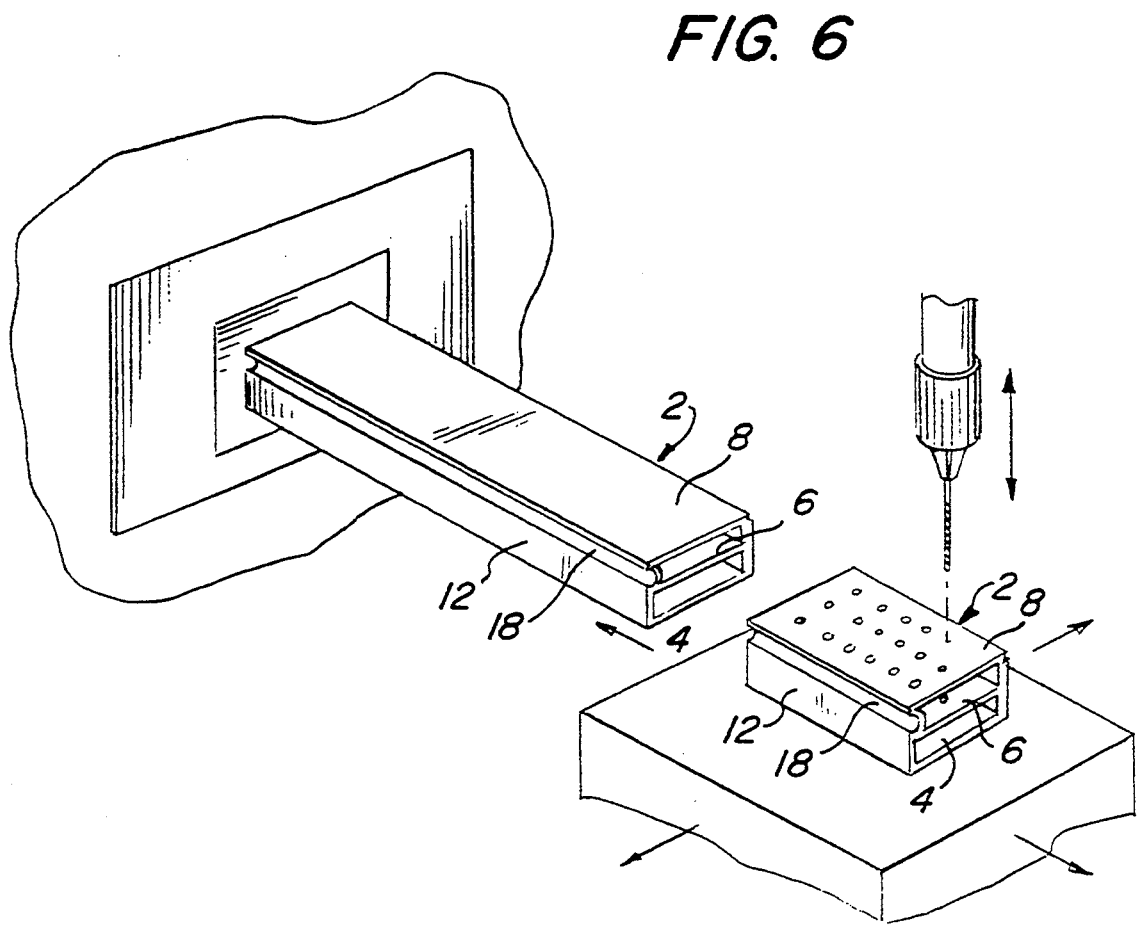
FIG. 6 is a perspective view of a drill press drilling support apertures into a base member.

The method of manufacturing the dental burs storage device is inexpensive and simple. As best shown in FIGS. 5 and 6, a molten material is entered into an extrusion mold which provides an extruded elongated base member 2, which is then cut by a blade saw into predetermined sections. The particular design of the storage device is particularly suitable to an extrusion process since each floor 4, 6, and 8 is parallel to the axle socket 18 of the extrusion.

A drill press is then used to drill a plurality of predetermined support apertures into the second support floor 8 and continue the drilling directly down through the first support floor 6.

Additional molten material is entered into a second mold which provides an extruded elongated lid 24, which is then cut into predetermined sections by a saw blade. The lids are then attached to the base members 2 by inserting the axle 32 attached to the end of the top back wall 26 of the lid 24 into a side of the axle socket 18 of the base member 2. The lids are reinforced to the base members 2 by a resilient pin 20 which is partly inserted into the ends of the axle 32 and wrapped through the base member 2 behind the axle socket 18 underneath the second support floor 8.

Those skilled in the art will appreciate that various adaptations and modifications of the just-described preferred embodiment can be configured without departing from the scope and spirit of the invention. Therefore, it is to be understood that, within the scope of the appended claims, the invention may be practiced other than as specifically described herein.

What is claimed is:

1. A storage device for dental burs comprising:
   a metal base member having three parallel support members integrally stacked above each other and having a first open space extending between a top support member and an intermediate support member and a second open space extending between the intermediate support member and a bottom support member, the top support member and the intermediate support member having a plurality of apertures juxtapositioned to receive and vertically support dental burs, the base member further including an integral first pivoting joint member on one side of the base member and an integral locking member on the other side of the base member;
   a metal lid member having a solid upper surface pivotally attached to the base member and extending parallel to the top support member when in a closed position, the metal lid member having an integral front wall terminating in a locking lip and an integral back wall terminating in a second pivoting joint member, the metal lid member capable of pivoting about the first and second pivoting joint members to enable a locking action of the locking member on the base member with the locking lip, the first pivoting joint member includes an elongated socket and the second pivoting joint member includes an axle of a dimension which is slidingly engaged for retention in the first pivoting joint member; and
   a resilient pin member that extends underneath the top support member and engages the respective ends of the axle to retain it within the elongated socket.

2. A storage device for dental burs comprising:
   a hollow base member having a first and second end, each end has an aperture, the hollow base member includes a first support floor with a plurality of support apertures that have a circumference size dimensioned to hold dental burs and a second support floor, parallel to the first support floor, with a plurality of support apertures that have a circumference size dimensioned to hold dental burs;
   means for removably restraining dental burs to prevent their release from the base member, whereby the dental burs can be washed and autoclaved in a sanitary manner while in a storage mode, including a lid with a top back wall which is pivotally fastened to the hollow base member, a top front wall parallel to the top back wall and detachable from the hollow base member, with a latch at a bottom edge of the top front wall permitting it to connect and disconnect with the hollow base member, and a solid ceiling member interconnecting the top front wall and top back wall that, when the lid is closed, is of a dimension above the hollow base member to fit dental burs inside the storage device and prevent the dental burs from falling out; and
   means for connecting the lid to the hollow base member including an axle attached to the top back wall, the hollow base member further includes an axle socket for pivotally holding the axle and a resilient pin which extends beneath the first support floor and is connected to the axle to lock it into the axle socket.

* * * * *